(12) United States Patent
Monty et al.

(10) Patent No.: US 7,104,111 B2
(45) Date of Patent: Sep. 12, 2006

(54) FORMATION OF METAL NANOWIRES FOR USE AS VARIABLE-RANGE HYDROGEN SENSORS

(75) Inventors: Greg Monty, Libertyville, IL (US); Kwok Ng, Austin, TX (US); Mohshi Yang, Austin, TX (US)

(73) Assignee: Nano-Proprietary, Inc., Austin, TX (US)

( * ) Notice: Subject to any disclaimer, the term of this patent is extended or adjusted under 35 U.S.C. 154(b) by 0 days.

(21) Appl. No.: 10/909,797

(22) Filed: Jul. 30, 2004

(65) Prior Publication Data

US 2005/0005675 A1 Jan. 13, 2005

Related U.S. Application Data

(62) Division of application No. 10/651,220, filed on Aug. 28, 2003, now Pat. No. 6,849,911.

(60) Provisional application No. 60/407,141, filed on Aug. 30, 2002.

(30) Foreign Application Priority Data

Aug. 29, 2003 (WO) ............... PCT/US03/27083

(51) Int. Cl.
*G01N 7/00* (2006.01)
(52) U.S. Cl. .......................... 73/23.2; 438/48
(58) Field of Classification Search ............. 73/23.2; 438/48
See application file for complete search history.

(56) References Cited

U.S. PATENT DOCUMENTS

| 4,240,879 A | 12/1980 | Dobson ................. 204/1 T |
| 5,670,115 A | 9/1997 | Cheng et al. ................. 422/90 |
| 6,120,835 A | 9/2000 | Perdieu ................. 427/125 |
| 6,359,288 B1 | 3/2002 | Ying et al. ................. 257/14 |
| 6,525,461 B1 | 2/2003 | Iwasaki et al. ............. 313/495 |
| 6,535,658 B1 | 3/2003 | Mendoza et al. ............ 385/12 |
| 2002/0079999 A1 | 6/2002 | Abdel-Tawab et al. ..... 336/208 |
| 2002/0117659 A1 | 8/2002 | Lieber et al. ................. 257/14 |
| 2003/0079999 A1 | 5/2003 | Penner et al. ............... 205/775 |
| 2003/0135971 A1 | 7/2003 | Liberman et al. .......... 29/419.1 |

OTHER PUBLICATIONS

J.N. Keuler et al., "Characterization of Electroless Plated Palladium-Silver Alloy Membranes," *Thin Solid Films*, 347 (1999), pp. 91-98.

V. Jayaraman et al., "Synthesis and Hydrogen Permeation Properties of Ultrathin Palladium-Silver Alloy Membranes," *Journal of Membrane Science*, 104 (1995), pp. 251-262.

(Continued)

*Primary Examiner*—Hezron Williams
*Assistant Examiner*—Rodney Frank
(74) *Attorney, Agent, or Firm*—Edward Mickelson; Kelly K. Kordzik; Winstead Sechrest & Minick P.C.

(57) ABSTRACT

The present invention provides for variable-range hydrogen sensors and methods for making same. Such variable-range hydrogen sensors comprise a series of fabricated Pd—Ag (palladium-silver) nanowires—each wire of the series having a different Ag to Pd ratio—with nanobreakjunctions in them and wherein the nanowires have predefined dimensions and orientation. When the nanowires are exposed to $H_2$, their lattace swells when the $H_2$ concentration reaches a threshold value (unique to that particular ratio of Pd to Ag). This causes the nanobreakjunctions to close leading to a 6–8 orders of magnitude decrease in the resistance along the length of the wire and providing a sensing mechanism for a range of hydrogen concentrations.

8 Claims, 5 Drawing Sheets

OTHER PUBLICATIONS

F.A. Lewis, *The Palladium Hydrogen System*, Academic Press, 1967, UT-Austin, QD 181, pp. 1-20 and pp. 48-51, 56-57, 70-71, 82-83, 86-87, 90-93112-113, 140-141, 144-145, 160-161.

E.C. Walter et al., "Sensors from Electrodeposited Metal Nanowires," *Surface and Interface Analysis*, 2002; 34: 409-412.

Frederic Favier et al., "Hydrogen Sensors and Switches from Electrodeposited Palladium Mesowire Arrays," *Science*, vol. 293, Sep. 21, 2001, pp. 2227-2234.

H.D. Tong et al., "A Hydrogen Separation Module Based on Wafer-Scale Micromachined Palladium-Silver Alloy Membranes," *IEEE, Transducers '03 The 12th* International Conference on Solid State Sensors, Actuators and Microsystems, Boston, Jun. 8-12, 2003, pp. 1742-1745.

Suleiman et al., "The effect of the cluster structure in the phase transition during hydrogen absorption", Annual Reports of Deutsches Elektronen-Synchroton (DESY) (2002).

Suleiman et al., "Pd-H Clusters: non-bulk like behavior", Annual Reports of Deutsches Elektronen-Synchroton (DESY) (2003).

Oh et al., "H NMR Study of Hydrogen in Palladium Nanocrystals", J. Korean Phys. Soc., 43(6) (Dec. 2003), pp. L958-962.

FORMATION OF METAL NANOWIRES FOR USE AS VARIABLE-RANGE HYDROGEN SENSORS

CROSS REFERENCE TO RELATED APPLICATIONS

The present application claims priority to the following U.S. Provisional Patent Application, Ser. No. 60/407,141, filed Aug. 30, 2002.

TECHNICAL FIELD

The present invention relates in general to the fabrication of metal nanowires, and in particular to hydrogen gas sensors comprising such nanowires.

BACKGROUND INFORMATION

Hydrogen gas ($H_2$) is widely used in industrial and laboratory settings. Because of its high-flamability in air, the need to detect hydrogen gas at levels below its lower explosive limit (LEL is 4% at 25° C.) is of considerable importance. The use of palladium (Pd) as a hydrogen sensor is well-established (F. A. Lewis, "The Palladium Hydrogen System," Academic Press, New York, 1967.) and based on the increased resistance realized when hydrogen dissolves into the metal creating a palladium hydride which has a lower degree of conductivity than pure palladium.

Recently, a palladium nanowire (also known as a "mesowire," where mesoscopic structures are characterized by a length scale ranging from the tens of nanometers to micometers) sensor has been described which operates with an inverse response, i.e., it realizes a decreased resistance when exposed to hydrogen (F. Favier, E. C. Walter, M. P. Zach, T. Benter, R. M. Penner "Hydrogen Sensors and Switches from Electrodeposited Palladium Mesowire Arrays," Science, 293, p. 2227–2231, 2001). Such nanowires are electrodeposited, from solutions of palladium chloride ($PdCl_2$) and perchloric acid ($HClO_4$), onto an electrically-biased graphite step ledge (presumably, these terraced step ledges produce an enhanced field leading to selective deposition). Once formed, these nanowires are transferred to an insulating glass substrate using a cyanoacrylate film. The diameters of these wires are reportedly as small as 55 nanometers (nm) and they possess gaps or break-junctions which impart them with high resistance. When hydrogen is introduced, a palladium-hydride ($PdH_x$) forms. At room temperature (25° C.), there is a crystalline phase change from $\alpha$ to $\beta$ when the concentration of hydrogen in air reaches 2% (15.2 Torr). Associated with this phase change is a corresponding 3–5% increase in the lattice parameter of the metal which leads to a "swelling" of the nanowire, thus bridging the nanogap breakjunctions (nanobreakjunctions) and leading to an overall decrease in the resistance along the length of the nanowire. The resistance change that occurs is between 6 and 8 orders of magnitude (typical devices see $1\times10^{-11}$ amps in the "off" state, and $1\times10^{-4}$ amps in the "on" state). This behavior is unique to nanowires possessing such nanogap breakjunctions. Fortunately, for sensor applications, these gaps re-open when the nanowires are removed from the hydrogen-containing environment, and the swollen nanowires revert back to their pre-swollen state.

The above-mentioned nanowire sensors have three primary deficiencies which can be improved upon. The first deficiency is the reliance on terraced graphite step ledges to form the nanowires. This limits the ability to pattern the nanowires into an arrangement of one's own choosing, i.e., it limits the length and orientation of the nanowires. The second deficiency lies with the need to transfer the nanowires from the conducting graphite surface to an insulating glass substrate using a cyanoacrylate "glue." Such transfer steps could damage the nanowires. Lastly, there are hydrogen concentration and temperature constraints which present, perhaps, the greatest deficiency in the current state of the art. At 25° C., for example, there is no $H_2$ concentration range over which this sensor can detect—merely a 2% threshold. By 50° C., this threshold moves up to 4–5% $H_2$ in air, which is above the lower explosive limit. Consequently, such nanowire sensors essentially provide only a hydrogen detection capability within a very narrow temperature range.

As a result of the foregoing, there is a need for a method that permits the ordered patterning of nanowires on a surface in a predefined way, and for a method that eliminates the need for the nanowires, once formed, to be transferred to another substrate. There is also a need for a method that overcomes the temperature/threshold concentration limitations of current hydrogen sensors and allows for a range of $H_2$ concentrations to be determined at any given temperature, and which allows for a wider range of operating temperatures such that the sensor is capable of detecting $H_2$ below its lower explosive limit. Such a device could serve as a variable or dynamic-range hydrogen sensor.

SUMMARY OF THE INVENTION

The present invention provides for variable-range hydrogen sensors and methods for making same. Such variable-range hydrogen sensors comprise one or more fabricated Pd—Ag (palladium-silver) nanowires—each wire having the same or a different Ag to Pd ratio—with nanobreakjunctions in them and wherein the nanowires have predefined dimensions and orientation. When the nanowires are exposed to $H_2$, their lattace swells when the $H_2$ concentration reaches a threshold value (unique to that particular ratio of Pd to Ag). This causes the nanobreakjunctions to close leading to a 6–8 orders of magnitude decrease in the resistance along the length of the wire and providing a sensing mechanism for a range of hydrogen concentrations.

The foregoing has outlined rather broadly the features and technical advantages of the present invention in order that the detailed description of the invention that follows may be better understood. Additional features and advantages of the invention will be described hereinafter which form the subject of the claims of the invention.

BRIEF DESCRIPTION OF THE DRAWINGS

For a more complete understanding of the present invention, and the advantages thereof, reference is now made to the following descriptions taken in conjunction with the accompanying drawings, in which:

FIGS. 2A and B illustrate an embodiment wherein chemical mechanical etching is used to generate metal electrodes (embedded in a dielectric surface) on which Pd or Pd-alloy nanowires can be electrochemically grown;

DETAILED DESCRIPTION

The present invention provides for a method of generating metal nanowires on a surface, wherein the nanowires are grown with predefined dimensions, compositions, and orientations. Such metal nanowires are termed "precisely-defined" herein. The present invention is also directed to a variable-range hydrogen sensor comprising one or more precisely-defined palladium-silver (Pd—Ag) nanowires of variable composition and possessing nanobreakjunctions which are closed at a composition-dependent hydrogen concentration threshold. In some embodiments, an array of such nanowires of differing composition is used. In such embodiments, the nanobreakjunctions close (in sequential fashion) as the concentration of $H_2$ is increased. Changes in an electrical property or properties (e.g., resistance) of these nanowires as a function of $H_2$ concentration present, permits the sensing of $H_2$ over a range of concentration. Such a variable-range sensor can even permit concentration determination when electrical responses of the sensor have been calibrated against known quantities of $H_2$. The precision with which this can be done is merely dependent upon the number of precisely-defined metal nanowires of different Pd:Ag ratios present in the sensor.

In some embodiments of the present invention, the precisely-defined nanowire sensors ("nanowire sensors") described herein are made by the electrochemical, electroless, or vapor deposition of metal into photolithographically-generated and etched channels within a dielectric material and which span two electrodes, permitting the generation of nanowires formed in any desired orientation, length, or arrangement, and without the need to transfer them to an additional substrate. Dimensions, in this embodiment are limited only by the dimensional limitations of photolithographic techniques, e.g., the wavelength of the radiation used.

Figure 1:
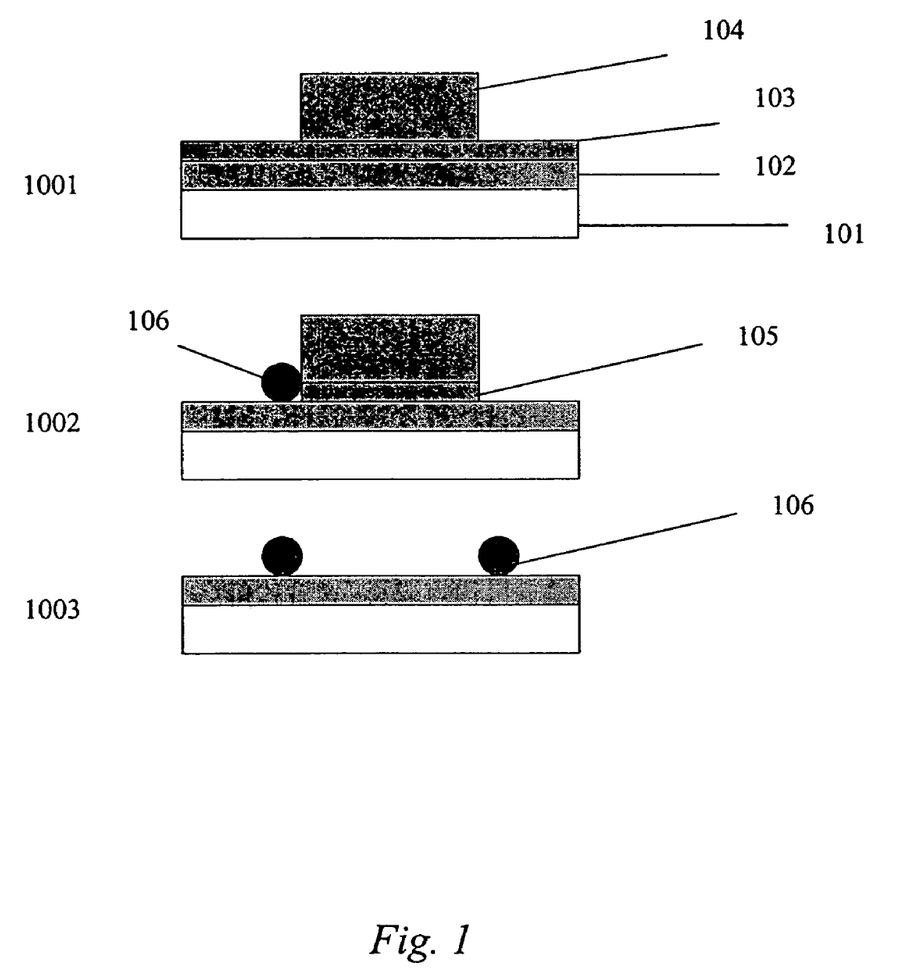
FIG. 1 illustrates an embodiment in which metal nanowires can be deposited on a substrate.

Referring to FIG. 1, in some embodiments, Pd nanowires are electrochemically deposited onto a $SiO_2$ dielectric substrate 102 (other embodiments employ different dielectric materials). In Step 1001, a 200–600 nm thick layer of silicon dioxide ($SiO_2$) 102 is plasma deposited on top of the base Si substrate 101. On top of this, Ti is thermally evaporated and condensed onto the surface such that a 10–100 nm (e.g., ~50 nm) Ti film 103 resides on top of the $SiO_2$ (note that in other embodiments Ti is sputtered or electron-beam evaporated onto the surface). A 1–5 µm (e.g., ~2 µm) Shipley AZ photoresist (PR) layer 104 is spin-coated onto the Ti film 103 using a spin coater operating at about 1000–5000 RPM. A subsequent baking process is used to remove the solvent. A photomask (essentially a glass plate with a photo-opaque design on it) is applied to the PR layer 104 and is exposed to UV light (e.g., generated by a mercury arc lamp or other source). The photomask is removed and the substrate is placed in a developer which removes the UV-exposed regions or the PR layer 104, thus creating a pattern in the PR layer 104. In Step 1002, the Ti layer 103 is etched using a reactive ion etching (RIE) plasma using a fluorine- or chlorine-containing gas (or other suitable etching process). This generates nanoscale "walls" (nanowalls) of Ti 105 which can then be electrically-biased such that Pd is electrochemically deposited (from a solution) along the Ti walls 105 as Pd nanowires 106 having diameters generally in the range of about 100 nm to about 700 nm, and perhaps smaller.

Methods for electrochemically depositing Pd from solution are well known in the art (F. Favier, E. C. Walter, M. P. Zach, T. Benter, R. M. Penner "Hydrogen Sensors and Switches from Electrodeposited Palladium Mesowire Arrays," Science, 293, p. 2227–2231, 2001). In Step 1003, the patterned photoresist 104 and the Ti walls 105 are removed to reveal the isolated nanowires 106. Variations on this embodiment include substituting carbon (C), tungsten (W), alloys of titanium and tungsten (TiW), and aluminum (Al) for the Ti, and electrochemically depositing nanowires of Pd-alloys like Pd—Ag. In this manner, nanowires of a variety of Pd:Ag ratios can be made.

Figure 2:
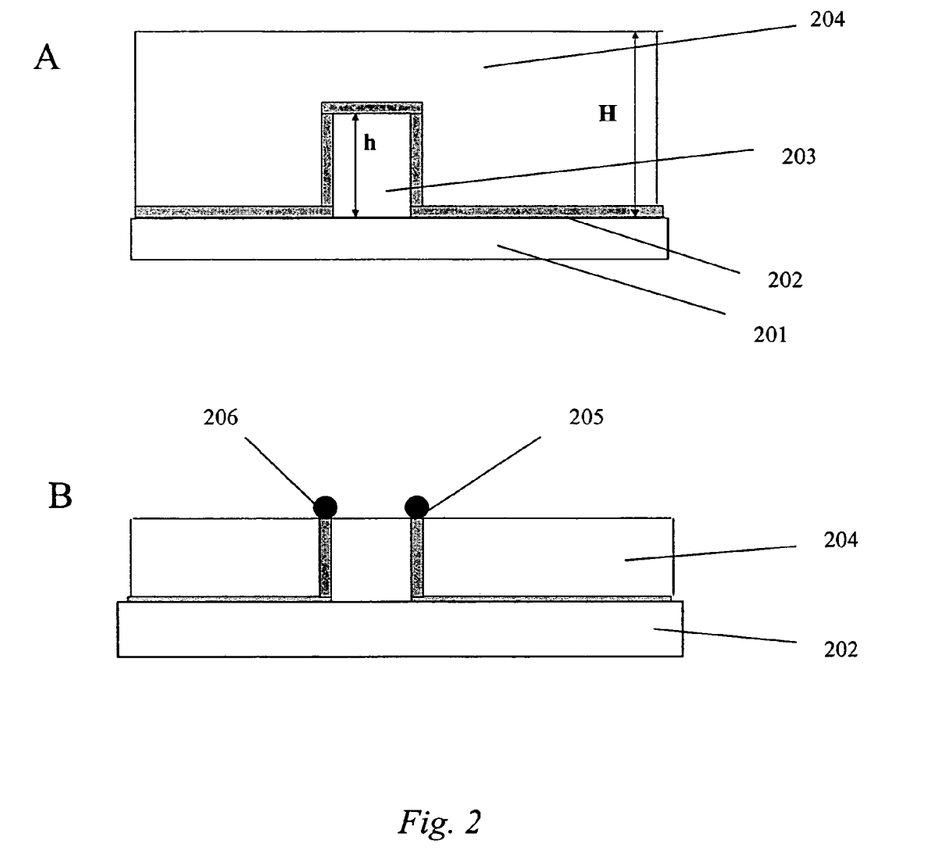

In another embodiment, shown in FIG. 2, small rectangular structures 203 of height h are formed from a dielectric material, e.g., $SiO_2$. These structures are placed on a surface 201, covered with a thin (~10 nm thick) metal layer 202 (e.g., Ni), then planarized with additional dielectric 204 to height H, as shown in FIG. 2A. Chemical-mechanical polishing (CMP) is then employed to etch away the dielectric material (from height H to below height h) and exposes the metal electrodes 205 on which the Pd or Pd-alloy nanowires 206 are grown, as shown in FIG. 2B. Variations on this embodiment include different dielectric materials, different metal thin films, size and shape of the dielectric structures, and where and how they are placed on the surface.

In another embodiment, polymethylmethacrylate (PMMA), or other suitable electron-beam resist material, is deposited on a conductive metal which has itself been deposited on a $SiO_2$ surface (or the surface of any dielectric material). Electron-beam (e-beam) lithography is then used to generate lines in the PMMA which can be as small as 20 nm in width. The conductive metal is then etched (via a RIE process) to replicate the PMMA pattern in the metal. The PMMA is removed and Pd or a Pd-alloy is electrodeposited onto the surface. The conductive metal can be optionally removed to maximize the performance of the hydrogen sensor.

One conductive "metal" ideally suited to the Application described in the preceding embodiment is carbon. In some embodiments, deposition of the PMMA onto a carbon-coated dielectric surface, lithographically patterning the PMMA with an electron beam, reactive ion etching of the exposed carbon, and removal of PMMA yields carbon nanoelectrodes along which Pd and Pd-alloy nanowires are grown. The carbon is then removed via RIE in either a hydrogen, oxygen, or air plasma. The carbon leaves as a volatile reaction product like methane ($CH_4$), carbon monoxide (CO), or carbon dioxide ($CO_2$)—depending on which reactive ion etch is used.

In another embodiment, PMMA is deposited directly onto an $SiO_2$ surface (or the surface of any dielectric material). Electron-beam lithography is then used to generate channels in the PMMA which can be as small as 20 nm in diameter. Pd or a Pd-alloy is then electrolessly-deposited onto the surface. Finally, the PMMA is removed with a suitable solvent to leave free-standing Pd or Pd-alloy nanowires on the surface.

In other embodiments of the present invention, carbon nanotubes (CNTs) are plated with a thin film of Pd or Pd-alloy using either an electrochemical or electroless plating process. Such thin films possess the same nanobreakjunctions that the other nanowires described herein do along the length of the CNTs. The underlying carbon (i.e., the carbon nanotubes) in these coated nanotubes is then removed via reactive ion etching, as described in the preceding paragraph, to yield Pd or Pd-alloy nanowires. In some of the embodiments utilizing carbon nanotubes, the CNT is grown in situ between two electrodes using an established vapor growth mechanism. Such a process, leads to the formation of some of the smallest Pd and Pd-alloy nanowire hydrogen sensors (CNTs can have diameters as small as 0.5 nm, but CNTs grown from a supported catalyst structure are usually larger). In other embodiments, the CNTs are produced external to the sensor device, then they are coated with Pd or a Pd-alloy. Such coated CNTs are then dispersed on a surface or in lithographically-generated channels bridging two electrodes on a surface. In these latter embodiments utilizing CNTs, the nanowire sensor is actually composed of a number of smaller nanowires.

Other embodiments of the present invention involve coating nanoparticles (having diameters as small as 1 nm) with a Pd and Pd-alloy. Silicon, silica, diamond, alumina, titania, or any other nanoparticle material is electrolessly plated with a Pd or Pd-alloy. These coated nanoparticles are then applied to a surface and made to bridge two electrodes using electrophoresis, spray methods, or pastes. Nanobreakjunctions exist in the coated surfaces and in the gaps (nanogaps) between adjacent particles. Variations on these embodiments include depositing such coated nanoparticles within lithographically-patterned channels on the surface of a dielectric material, and generating nanoparticles of Pd and Pd-alloys electrochemically on a surface.

In all embodiments involving nanoparticles, the nanoparticles are deposited or applied to a surface in such a way so as to assure that there is significant contact between nanoparticles. This ensures that electrical contact is made throughout the entire nanoparticle network. As in the electrochemically-generated Pd and Pd-alloy wires, it is still the nanobreakjunctions on the surface of the coated particles which serve in the sensing mechanism. Here, the nanowires are simply created with numerous coated nanoparticles.

Other embodiments include depositing Pd and Pd-alloys using thermal- or electron-beam evaporation. Furthermore, nanowires of any platable metal or combination of platable metals can be made using either electrochemical or vapor deposition techniques. Platable metals include, but are not limited to, Ag, Au, Cu, Co, Fe, Ni, Pd, Pt, Cr, Zn, Sn, Ti, and combinations thereof. As will be appreciated by those of skill in the art, countless other variations exist utilizing maskless or laser photolithographic techniques and combinations of all the previously mentioned techniques.

The nanowires of the present invention can also be patterned on a surface to have specific dimensions and orientations. This is important because future commercialization of this technology will likely depend on the ability to control the size, shape, and orientation of the nanowires within a manufacturing context.

The above-described processes of making metal nanowires provide numerous advantages over the existing prior art, particularly for fabricating hydrogen sensors. The number, length, diameter, and orientation of nanowires in the device can all be controlled by lithography. The electroplating (deposition) process can be more easily controlled because one knows exactly the length and number of wires and therefore can control the size of the nanowires more easily. All the nanowires can be aligned in parallel (if desired), whereas the prior art does not have any control over this on a graphite surface. Much of the technology of the present invention is built on Si which is easily cleaved/sawed into individual devices, rather than being on glass which is difficult to work with. Furthermore, no glue (cyanoacrylate) is required in the processes of the present invention. Such glue has limited use over a temperature range, and typically has a thermal coefficient of expansion which is may further limit its use over a range of temperatures.

In general, the present invention also comprises any method that allows for the creation and controlled placement of Pd and Pd-alloy (e.g., Pd—Ag) nanowires for use as hydrogen sensors. The invention also provides for variable-range hydrogen sensors in that it provides a method for preparing nanowires which are sensitive to hydrogen over a range of concentrations at a given temperature and to a given $H_2$ concentration over a range of temperatures. This is accomplished by alloying the Pd with Ag and forming nanowires of this Pd—Ag alloy as described above. Like the Pd nanowires, such Pd—Ag nanowires possess nanobreakjunctions which are responsive to $H_2$ concentration. Alloying Pd with Ag permits one to modulate the $\alpha$-$\beta$ transition and enables the sensor to respond (by closing the nanobreakjunctions) to a much wider range of temperatures and $H_2$ concentrations. Methods of electrochemically (J. N. Keuler, L. Lorenzen, R. D. Sanderson, V. Prozesky, W. J. Przybylowicz "Characterization of electroless plated palladium-silver alloy membranes," Thin Solid Films, 347, p. 91–98, 1999) and evaporatively (V. Jayaraman, Y. S. Lin "Synthesis and hydrogen permeation properties of ultrathin palladium-silver alloy membranes," J. Membrane Sci., 104, p. 251–262, 1995) alloying Ag with Pd are well-established. The invention also provides a method of making sensors comprising of an array of several (2 or more) metal nanowires, each possessing a different Pd/Ag ratio, where the amount of Ag can vary from about 0% to about 26%. Not intending to be bound by theory, other platable metals and combinations of platable metals may also be used to make nanowire sensors for hydrogen and, perhaps, other gases. The key here is that such nanowires comprise nanobreakjunctions which close at some threshold hydrogen concentration.

Figure 3:
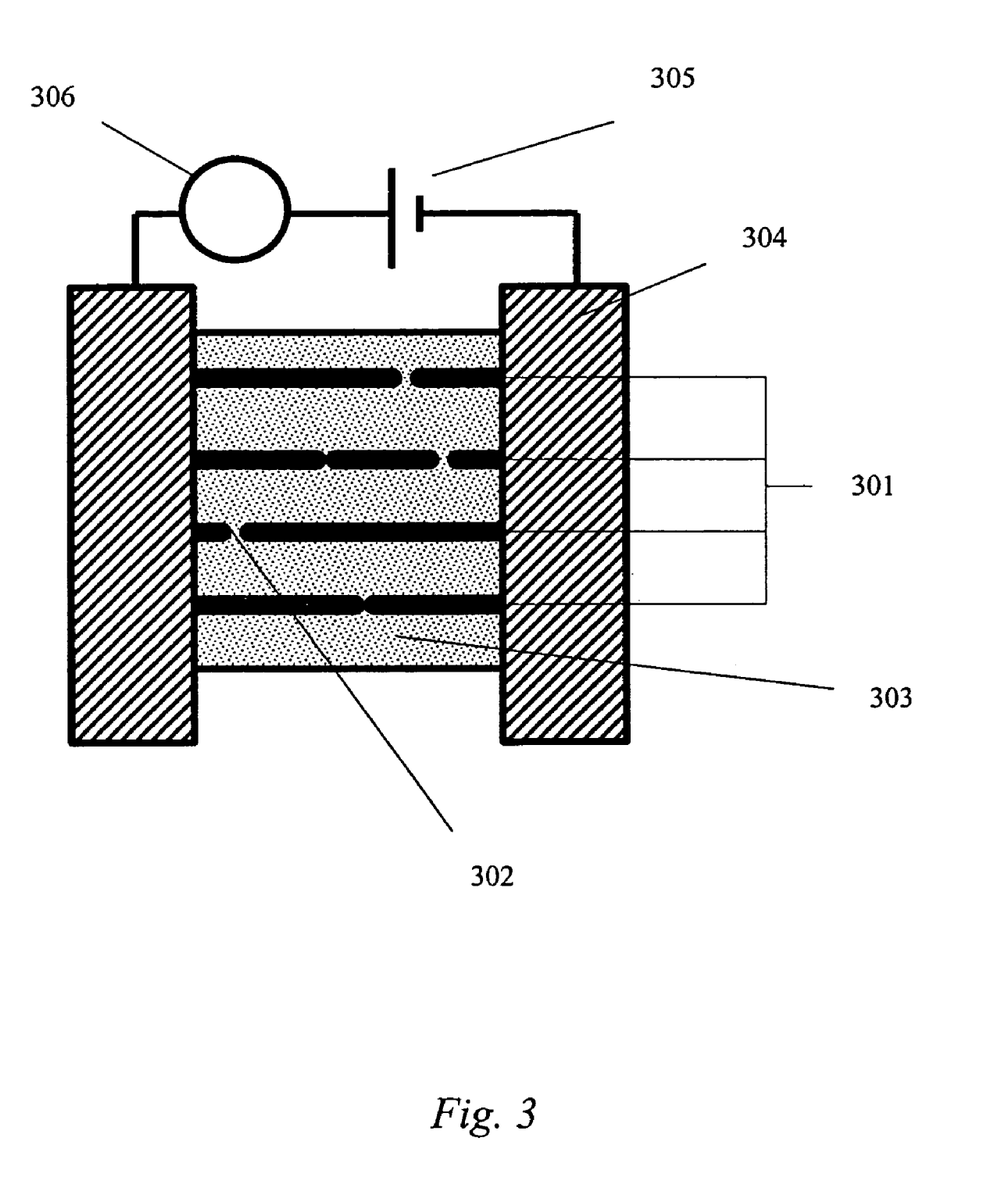
FIG. 3 illustrates a variable-range hydrogen sensor of the present invention comprising metal nanowires.

FIG. 3 illustrates a variable-range hydrogen sensor of the present invention comprising metal nanowires. Referring to FIG. 3, metal alloy nanowires 301 of variable composition and comprising nanobreakjunctions 302 are present on a dielectric surface 303. An electric circuit comprising the nanowires 301 is formed with electrical contacts of metal film 304 and a power supply 305. The sensor functions by monitoring some electrical property of the nanowires with a monitoring device 306 (e.g., an amp meter) for changes as the nanowires are exposed to hydrogen.

Figure 4:
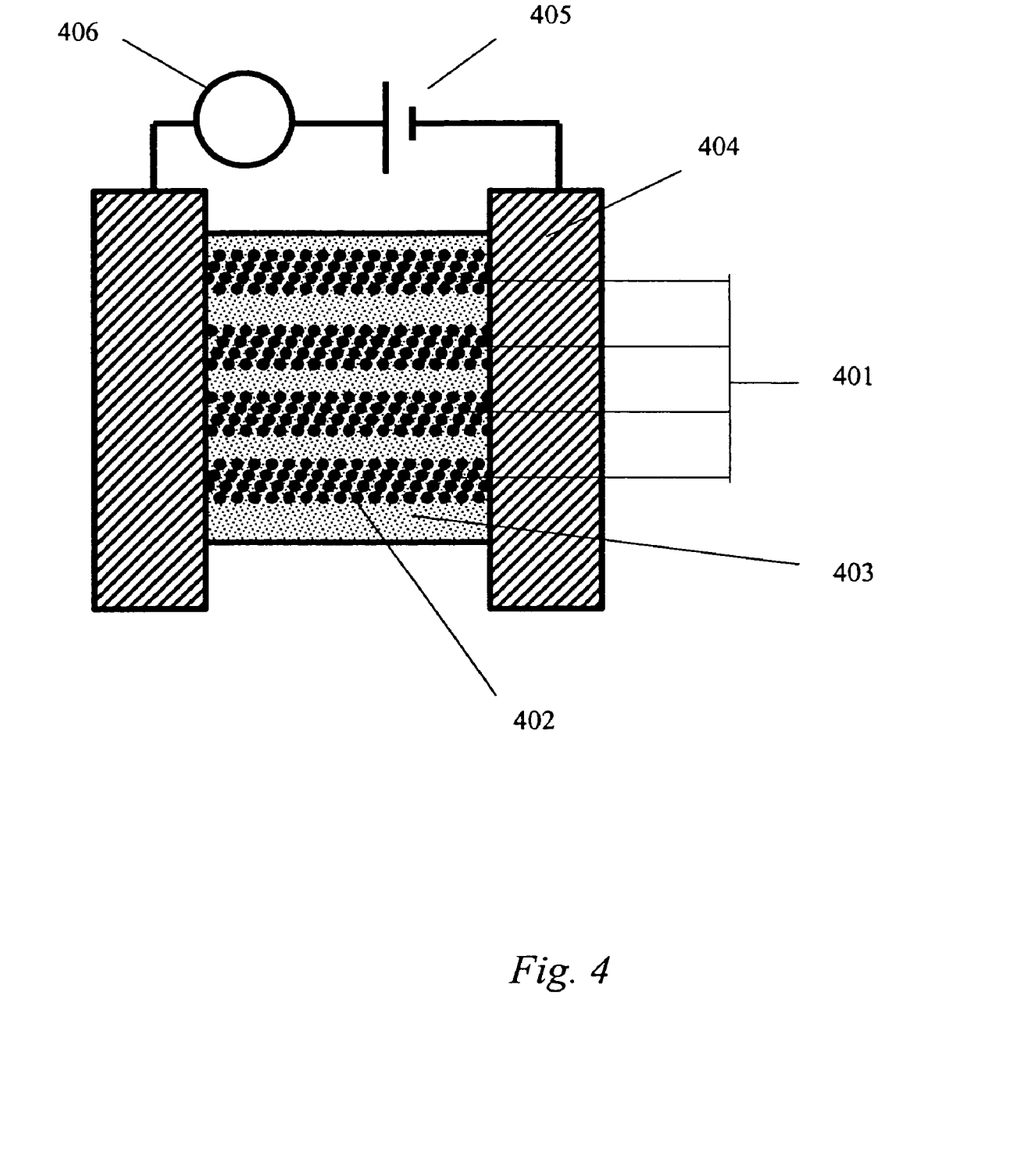
FIG. 4 illustrates a variable-range hydrogen sensor of the present invention comprising columns of metal nanoparticles.

FIG. 4 illustrates a variable-range hydrogen sensor of the present invention comprising columns of metal nanoparticles. Referring to FIG. 4, columns of metal alloy nanoparticles 401 of variable composition and comprising nanobreakjunctions and nanogaps 402 are present on a dielectric surface 403. An electric circuit comprising the columns of metal alloy nanoparticles 401 is formed with electrical contacts of metal film 404 and a power supply 405. The sensor functions by monitoring some electrical property of the nanowires with a monitoring device 406 (e.g., an amp meter) for changes as the columns of nanoparticles are exposed to hydrogen.

An advantage to alloying Pd with Ag in the nanowires is that it permits the formation of hydrogen sensors having a variable-range of detection points. Using pure Pd nanowires, one is limited only to about a 2% detection capability at room temperature, and at 40–50° C., the $\alpha$-$\beta$ transition point shifts to 4–5% $H_2$, above the point at which it is useful in detecting explosive $H_2$ levels. This limitation is overcome by making nanowire alloys of Pd—Ag in the 0–26% weight concentration of Ag to Pd. As mentioned above, such nanowire alloys will permit hydrogen detection over a wide range of temperatures and hydrogen concentrations. Furthermore, using an array of different Pd—Ag nanowires (multiple nanowires, each having a different Pd to Ag ratio) allows for the formation of a variable-range hydrogen sensor which will be dramatically more useful in research and industrial settings.

Additionally, as an alternative to basing the sensing mechanism on a sharp change in resistance, the hydrogen sensing process can also be made to work on changes in capacitance or conductance. Essentially, monitoring any electrical property which changes in a pre-defined manner as a result of closing the nanobreakjunctions within the nanowire can be used to sense an increase in the hydrogen concentration of the surrounding environment.

Figure 5:
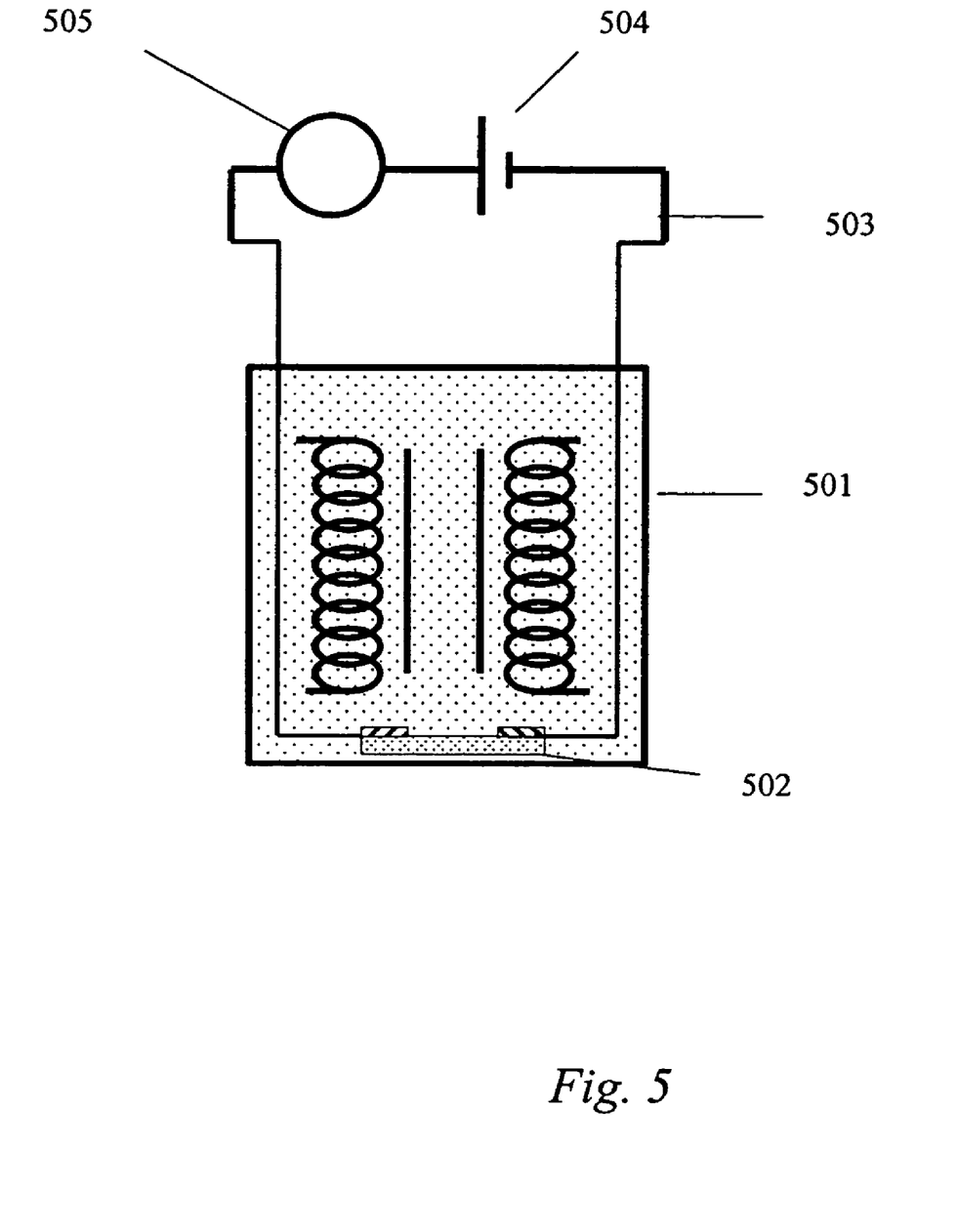
FIG. 5 illustrates an embodiment wherein a variable-range hydrogen sensor of the present invention is used to monitor hydrocarbon breakdown in electrical transformers.

An exemplary application for such hydrogen sensors is in the monitoring of hydrocarbon breakdown (which leads to the evolution of hydrogen) in transformers. FIG. 5 illustrates a placement of such a sensor 502 in a transformer 501 for hydrogen monitoring, wherein electrical contacts 503 connect the sensing element 502 (comprising nanowires or columns of metal nanoparticles) to a power supply 504 and an electrical property monitoring device 505. In some embodiments, the sensor 502 is placed in the transformer such that it is exposed to transformer oil. When the filled transformer operation becomes defective, hydrogen and other dissolved gases form in the oil. The sensor 502 monitors the $H_2$ content dissolved in the oil, helping to identify potential breakdowns and permitting maintenance before such breakdown occurs. Such monitoring can serve to economize the maintenance and downtime involved in operating such transformers by providing for a realtime and remote monitoring means.

Although the present invention and its advantages have been described in detail, it should be understood that various changes, substitutions and alterations can be made herein without departing from the spirit and scope of the invention as defined by the appended claims.

What is claimed is:

1. A method comprising the steps of:
   a) forming, using lithographic and electrochemical deposition means, at least one precisely-defined metal-alloy nanowire comprising nanobreakjunctions which close when exposed to predefined threshold concentrations of hydrogen;
   b) forming a circuit comprising said nanowire; and
   c) monitoring an electrical property within said circuit so as to determine when said nanobreakjunctions close.

2. The method of claim 1, wherein the nanowire comprises Pd and Ag.

3. The method of claim 1, wherein the metal nanowires have a composition that can be tailored so as to effect nanobreakjunction closure at varying concentrations of hydrogen.

4. The method of claim 1, wherein said method provides for hydrogen detection in transformers.

5. A method comprising the steps of:
   a) forming, using lithographic and electroless deposition means, at least one precisely-defined metal-alloy nanowire comprising nanobreakjunctions which close when exposed to predefined threshold concentrations of hydrogen;
   b) forming a circuit comprising said nanowire; and
   c) monitoring an electrical property within said circuit so as to determine when said nanobreakjunctions close.

6. The method of claim 5, wherein the nanowire comprises Pd and Ag.

7. The method of claim 5, wherein the metal nanowires have a composition that can be tailored so as to effect nanobreakjunction closure at varying concentrations of hydrogen.

8. The method of claim 5, wherein said method provides for hydrogen detection in transformers.

* * * * *